United States Patent
Li et al.

(10) Patent No.: US 8,445,868 B2
(45) Date of Patent: May 21, 2013

(54) OLIGOFLUORANTHENES AND METHODS AND APPARATUSES FOR DETECTING NITROAROMATICS USING THE SAME

(75) Inventors: Xin-gui Li, Shanghai (CN); Yaozu Liao, Shanghai (CN); Mei-rong Huang, Shanghai (CN)

(73) Assignee: Tongji University, Shanghai (CN)

( * ) Notice: Subject to any disclaimer, the term of this patent is extended or adjusted under 35 U.S.C. 154(b) by 0 days.

(21) Appl. No.: 13/503,349

(22) PCT Filed: Mar. 14, 2011

(86) PCT No.: PCT/CN2011/071760
§ 371 (c)(1),
(2), (4) Date: Apr. 20, 2012

(87) PCT Pub. No.: WO2012/122699
PCT Pub. Date: Sep. 20, 2012

(65) Prior Publication Data
US 2012/0280145 A1    Nov. 8, 2012

(51) Int. Cl.
*G01N 21/64*    (2006.01)

(52) U.S. Cl.
USPC ........................................ 250/459.1

(58) Field of Classification Search
USPC ........................................ 250/458.1
See application file for complete search history.

(56) References Cited

U.S. PATENT DOCUMENTS

| 6,004,685 | A  | 12/1999 | Antoniadis et al. |
| 6,127,516 | A  | 10/2000 | Bard et al. |
| 6,322,910 | B1 | 11/2001 | Arai et al. |
| 7,183,010 | B2 | 2/2007 | Jarikov |
| 7,488,856 | B2 | 2/2009 | Schwalm et al. |
| 2008/0213623 | A1 | 9/2008 | Dotz |

FOREIGN PATENT DOCUMENTS

| CN | 101328255 A | 12/2008 |
| GB | 2463040 A | 3/2010 |
| WO | WO 2010/023443 A2 | 3/2010 |

OTHER PUBLICATIONS

Akcelrud, "Electroluminescent polymers," 2003, Progress in Polymer Science, vol. 28, pp. 875-962.*
Schlicke et al, "Repetitive Synthesis of soluable oligofluoranthene derivatives and deir electrochemical analysis," 1996, Synlett, Letters, pp. 425-426.*
Fan, et al., "Electrochemical polymerization of anthracene in boron trifluoride diethyl etherate," *Journal of Electroanalytical Chemistry*, 575, 287-292, 2005.
Germain, et al., "Optical explosives detection: from color changes to fluorescence turn-on," *Chem. Soc. Rev.*, 2009, 38, 2543-2555.
Ghosh, et al., "Self-Assembly of a Nanoscopic Prism via a New Organometallic Pt3 Acceptor and Its Fluorescent Detection of Nitroaromatics," *Organometallics* 2008, 27, 316-319.

(Continued)

*Primary Examiner* — Kiho Kim
(74) *Attorney, Agent, or Firm* — Knobbe, Martens, Olson & Bear LLP

(57) ABSTRACT

The present application relates to compositions having at least one oligofluoranthene. The compositions may, for example, emit blue or green light when exposed to a blue or ultraviolet radiation. Methods of making the compositions are also disclosed, as well as methods and apparatuses for producing light and detecting nitroaromatics using the compositions.

20 Claims, 9 Drawing Sheets

OTHER PUBLICATIONS

He, et al., "A novel picric acid film sensor via combination of the surface enrichment effect of chitosan films and the aggregation-induced emission effect of siloles," *J. Mater.Chem.*, 19, 7347-7353, 2009.

Hu, et al., "A selective optical sensor for picric acid assay based on photopolymerization of 3-(N-methacryloyl) amino-9-ethylcarbazole," *Analytica Chimica Acta*, 570, 170-175, 2006.

Kawano, et al., "Blue-Emitting Poly(2,7-pyrenylene)s: Synthesis and Optical Properties," *Macromolecules*, 41(21), 7933-7937, 2008.

Kertesz, et al., "Electronic Structure of Polyfluoranthene Ladder Polymers," *Macromolecules* 1996, 29, 940-945.

Li, et al., "Functionalized Siloles: Versatile Synthesis, Aggregation-Induced Emission, and Sensory and Device Applications," *Adv. Funct. Mater.* 2009, 19, 905-917.

Li, et al., "Simple Efficient Synthesis of Strongly Luminescent Polypyrene with Intrinsic Conductivity and High Carbon Yield by Chemical Oxidative Polymerization of Pyrene, " *Chem. Eur. J.*, 16, 4803-4813, 2010.

Lu, et al., "A reusable optical sensing layer for picric acid based on the luminescence quenching of the Eu-thenoyltrifluoroacetone complex," *Analytica Chimica Acta* 318 (1996) 175-179.

Lu, et al., "Electrochemical polymerization of pyrene in the electrolyte of boron trifluoride diethyl etherate containing trifluoroacetic acid and polyethylene glycol oligomer," *Journal of Electroanalytical Chemistry* 586, 154-160, 2006.

Marciniak, B., "The growth, morphology and perfection of fluoranthene crystals grown from supercooled chlorine derivative solutions on spontaneously formed seeds," *Journal of Crystal Growth*, 236, 333-346, 2002.

Mori, et al., "Synthesis and optical properties of polynaphthalene derivatives," *Optical Materials*, 30, 545-552, 2007.

Nöll, et al., "Electronic Structure and Properties of Poly- and Oligoazulenes," *J. Phys. Chem. C* 112, 2156-2164, 2008.

Ni et al., "An anthracene/porphyrin dimer fluorescence energy transfer sensing system for picric acid," *Talanta* 63, 251-257, 2004.

Niu, et al., "Covalently immobilized aminonaphthalimide as fluorescent carrier for the preparation of optical sensors," *Anal Bioanal Chem* (2002) 372 :519-524.

Qin, et al- "Polytriazoles with Aggregation-Induced Emission Characteristics: Synthesis by Click Polymerization and Application as Explosive Chemosensors," *Macromolecules* 2009, 42, 1421-1424.

Sanchez, et al., "Synthesis, Luminescence Properties, and Explosives Sensing with 1,1-Tetraphenylsilole- and 1,1-Silafluorene-vinylene Polymers," *Chem. Mater.* 2007, 19, 6459-6470.

Sanchez, et al., "Efficient blue-emitting silafluorene-fluorine-conjugated copolymers: selective turn-off/turn-on detection of explosives," *J. Mater. Chem.*, 2008, 18, 3143-3156.

Saxena, et al., "Fluoroalkylated Polysilane Film as a Chemosensor for Explosive Nitroaromatic Compounds," *Chem. Mater.* 2005, 17, 2181-2185.

Schlüter, et al., "Synthesis of a fully unsaturated all-carbon ladder polymer," *Nature*, vol. 368, 831-834, 1994.

Shiraishi, et al., "Trace Detection of Explosive Particulates with a Phosphole Oxide," *ACS Applied Materials & Interfaces*, 2009, vol. 1, No. 7, 1379-1382.

Sohn, et al., "Detection of TNT and Picric Acid on Surfaces and in Seawater by Using Photoluminescent Polysiloles," *Angew. Chem.* 2001, 113, Nr. 11, 2162-2163.

Sohn, et al, "Detection of Nitroaromatic Explosives Based on Photoluminescent Polymers Containing Metalloles," *J. Am. Chem. Soc.* 2003, 125, 3821-3830.

Waltman, et al., "The Electrochemical Oxidation and Polymerization of Polycyclic Hydrocarbons," *J. Electrochem. Soc.*, vol. 132, No. 3, 631-634, 1985.

Waltman, et al., "Electrically conducting polymers: a review of the electropolymerization reaction, of the effects of chemical structure on polymer film properties, and of applications towards technology," *Can. J. Chem.*, 1986, vol. 64, 76-95.

Xu, et al., "Electrochemical Polymerization of Fluoranthene and Characterization of Its Polymers," *J. Phys. Chem.* B 2006, 110, 2643-2648.

Yamamoto, et al., "Synthesis of $\pi$-conjugated polymers bearing electronic and optical functionalities by organometallic polycondensations and their chemical properties," *Polymer* 48, 5449-5472, 2007.

Yang, et al., "Picric acid sensitive optode based on a fluorescence carrier covalently bound to membrane," *Analyst*, 2001, 126, 349-352.

Yang, et al., "A selective PVC membrane for di- or trinitrophenol based on N,N-dibenzyl-3,3',5,5'-tetramethylbenzidine," *Analyst*, 127, 119-124, 2002.

Zhang, et al., "Phenothiazine-based oligomers as novel fluorescence probes for detecting vapor-phase nitro compounds," *Talanta* 82 (2010) 1943-1949.

Zhou, et al., "Electrochemical polymerization of phenanthrene in mixed electrolytes of boron trifluoride diethyl etherate and concentrated sulfuric acid," *Polym. Int.* 57:92-98, 2008.

International Search Report received in PCT/CN2011/071760, mailed Dec. 29, 2011.

\* cited by examiner

OLIGOFLUORANTHENES AND METHODS AND APPARATUSES FOR DETECTING NITROAROMATICS USING THE SAME

CROSS-REFERENCE TO RELATED APPLICATIONS

This application is the U.S. National Phase under 35 U.S.C. §371 of International Application No. PCT/CN2011/071760, filed Mar. 14, 2011. The International Application was filed in English. The contents of the International Application are hereby incorporated by reference in their entirety.

BACKGROUND

Methods for identifying and detecting nitroaromatic compounds, such as picric acid (PA), 2,4,6-trinitrotoluene (TNT), 2,4-dinitrotoluene (DNT), 1,3,5-trinitrobenzene (TNB), and 2,6-dinitrobenzonitrile (DNB), at trace levels are desirable for various applications, such as environmental science, public security, and forensics. Various methods exist for detecting nitroaromatics. These methods include gas chromatography coupled with mass spectrometry, surface enhanced Raman spectroscopy, nuclear quadrupole resonance, energy dispersive X-ray diffraction, neutron activation analysis, electron capture detection, and ion mobility spectrometry (IMS).

SUMMARY

Some embodiments disclosed herein include a composition having one or more oligofluoranthenes, where the one or more oligofluoranthenes each independently include at least two fluoranthene units represented by Formula I:

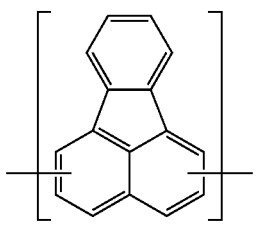
(I)

wherein at least one oligofluoranthene in the composition is not periflanthene.

In some embodiments, at least one of the one or more oligofluoranthenes includes at least three fluoranthene units represented by Formula I.

In some embodiments, at least one of the one or more oligofluoranthenes includes at least two fluoranthene units selected from a first unit represented by Formula II, a second unit represented by Formula III, and combinations thereof:

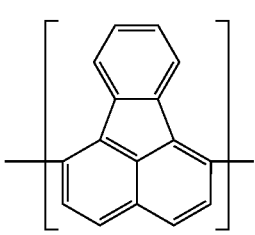
(II)

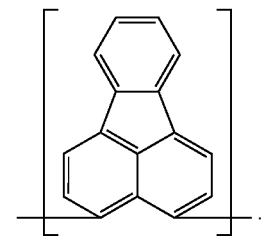
(III)

In some embodiments, at least one of the one or more oligofluoranthenes has a molecular formula selected from the group consisting of $C_{32}H_{16}$, $C_{48}H_{24}$, and $C_{80}H_{40}$. In some embodiments, at least one of the one or more oligofluoranthenes has a molecular formula of $C_{32}H_{16}$. In some embodiments, wherein at least one of the one or more oligofluoranthenes includes a compound represented by Formula IV:

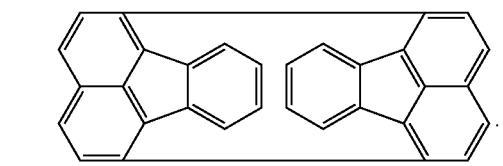
(IV)

In some embodiments, at least one of the one or more oligofluoranthenes has a molecular formula of $C_{80}H_{40}$. In some embodiments, at least one of the one or more oligofluoranthenes includes a compound represented by Formula V:

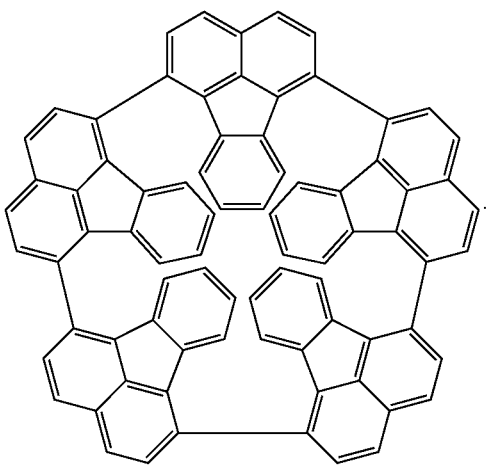
(V)

In some embodiments, at least one of the one or more oligofluoranthenes includes a compound represented by Formula VI:

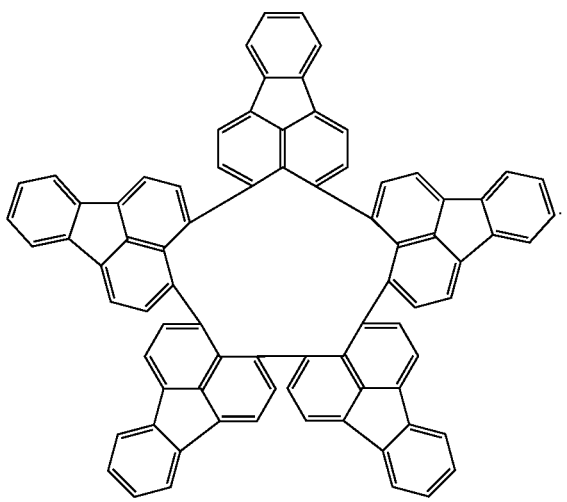

(VI)

In some embodiments, at least one of the one or more oligofluoranthenes has a molecular formula of $C_{48}H_{24}$. In some embodiments, at least one of the one or more oligofluoranthenes includes a compound represented by Formula VII:

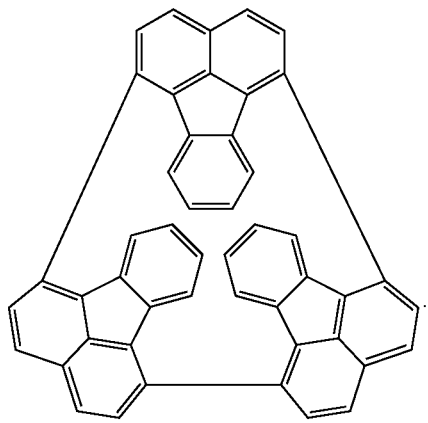

(VII)

In some embodiments, the composition comprises at least about 1 ppm of the one or more oligofluoranthenes.

In some embodiments, the composition exhibits a peak emission wavelength of about 450 nm to about 550 nm when exposed to ultraviolet or violet radiation.

In some embodiments, the composition exhibits an electrical conductivity of at least $10^{-9}$ S·cm$^{-1}$ when doped with an effective amount of a dopant. In some embodiments, the dopant is iodine.

In some embodiments, the composition exhibits a peak emission intensity that is at least five times greater than a peak emission intensity for fluoranthene when exposed to ultraviolet or violet radiation.

In some embodiments, the composition includes at least 50% by weight of an inert polymer. In some embodiments, the inert polymer is polysulfone.

Some embodiments disclosed herein include a method of making a composition, the method includes: forming a composition including an oxidizing agent and fluoranthene; and maintaining the composition under conditions effective to covalently bond two or more fluoranthenes to form one or more oligofluoranthenes.

In some embodiments, the one or more oligofluoranthenes each independently include at least two fluoranthene units represented by Formula I:

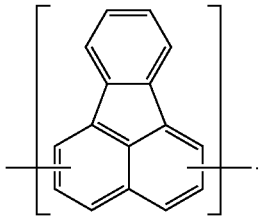

(I)

In some embodiments, the molar ratio of the oxidizing agent to fluoranthene in the composition is less than or equal to about 15:1. In some embodiments, the molar ratio of the oxidizing agent to fluoranthene in the composition is at least about 3:1.

In some embodiments, the composition is maintained at a temperature of about 30° C. to about 70° C.

In some embodiments, at least one of the one or more oligofluoranthenes has a molecular formula selected from $C_{32}H_{16}$, $C_{48}H_{24}$, and $C_{80}H_{40}$.

In some embodiments, the method yields at least about 40% by weight of the one or more oligofluoranthenes relative to a total amount of fluoranthene in the composition.

In some embodiments, at least about 90% by weight of a total amount of aromatic organic compounds in the composition are fluoranthene.

Some embodiments disclosed herein include an apparatus including: at least one light source configured to emit an ultraviolet or violet radiation; and a composition configured to receive at least a portion of the radiation emitted from the light source, wherein the composition includes one or more oligofluoranthenes, wherein the one or more oligofluoranthenes each independently include at least two fluoranthene units represented by Formula I:

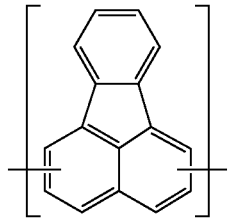

(I)

wherein at least one oligofluoranthene in the composition is not periflanthene.

In some embodiments, at least one light detector configured to measure light emitted from the composition is included.

In some embodiments, a housing is included, where the housing contains the composition and is configured to receive a sample adjacent to the composition.

Some embodiments disclosed herein include an organic light-emitting diode including: at least one light-emitting active layer; at least one conducting layer on one side of the light-emitting active layer; at least one cathode; and at least one anode, where the light-emitting active layer and conducting layer are disposed between the cathode and the anode, and the light-emitting active layer includes one or more oligofluoranthenes, wherein the one or more oligofluoranthenes each independently include at least two fluoranthene units represented by Formula I:

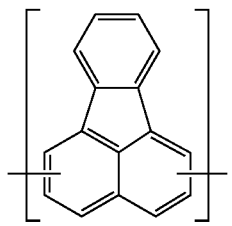

(I)

wherein at least one oligofluoranthene in the composition is not periflanthene.

Some embodiments disclosed herein include a method of producing light including exposing a composition to a violet or ultraviolet radiation, where the composition includes one or more oligofluoranthenes, wherein the one or more oligofluoranthenes each independently include at least two fluoranthene units represented by Formula I:

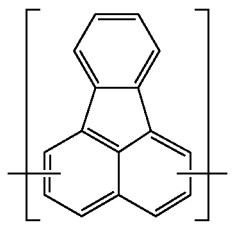

(I)

wherein at least one oligofluoranthene in the composition is not periflanthene.

Some embodiments disclosed here include a method for detecting nitroaromatics within a sample, the method including: providing a sample suspected of containing one or more nitroaromatics; contacting the sample with a composition comprising one or more oligofluoranthenes, where the one or more oligofluoranthenes each independently include at least two fluoranthene units represented by Formula I:

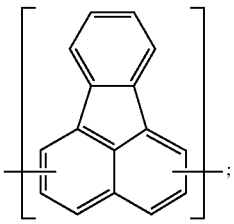

(I)

exposing the composition to a radiation effective to produce fluorescence from the composition; and measuring the amount of fluorescence produced by the composition.

In some embodiments, the produced fluorescence is greater in the absence of nitroaromatics than in the presence of nitroaromatics.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
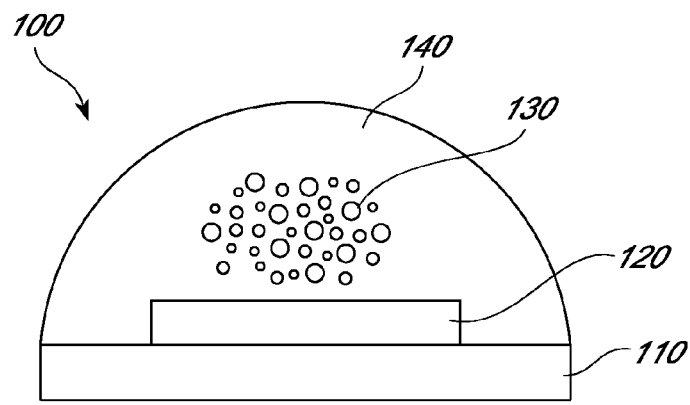
FIG. 1 depicts an illustrative embodiment of a lighting apparatus that is within the scope of the present application (not to scale).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Disclosed herein are compounds including one or more oligofluoranthenes. These compounds may, for example, exhibit superior fluorescence properties. The compounds may also provide, in some embodiments, highly sensitive detection of nitroaromatics. The present application also relates to methods of making these compounds, method of using these compounds, and apparatuses that include these compounds.

Compositions Including Oligofluoranthenes

Some embodiments disclosed herein include a composition having one or more oligofluoranthenes. The one or more oligofluoranthenes may, for example, each independently include, at least two fluoranthene units represented by Formula I:

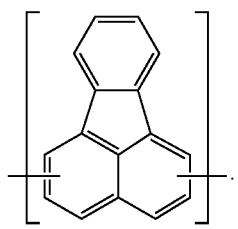

(I)

In some embodiments, at least one oligofluoranthene in the composition is not periflanthene.

For purposes of the present application, the nomenclature for fluoranthene units within the oligofluoranthene is shown below:

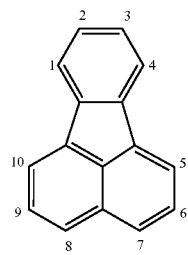

As noted above, the oligofluoranthenes can include two or more fluoranthene units. The two or more fluoranthene units may be linked together to form the oligofluoranthene. In some embodiments, the oligofluoranthene includes at least two fluoranthene units that are covalently bonded together by one or two carbon-carbon bonds. For example, an oligofluoranthene may include two fluoranthene units with a covalent bond between the 5- and 10-positions on the respective fluoranthene unit. This example of an oligofluoranthene may be referred to as a cyclic dimer having two fluoranthene units.

In some embodiments, at least a portion of the fluoranthene units (e.g., two, three, four, five, six, seven, or more fluoranthene units) in the oligofluoranthene each have one, two, or more carbon-carbon bonds linking with other fluoranthene units. In some embodiments, all of the fluoranthene units in the oligofluoranthene each include, one, two, or more carbon-carbon bonds linking with other fluoranthene units. As one example, the oligofluoranthene represented by Formula V includes five fluoranthene units that each include carbon-carbon bonds at the 5- and 10-positions which link to two other fluoranthene units:

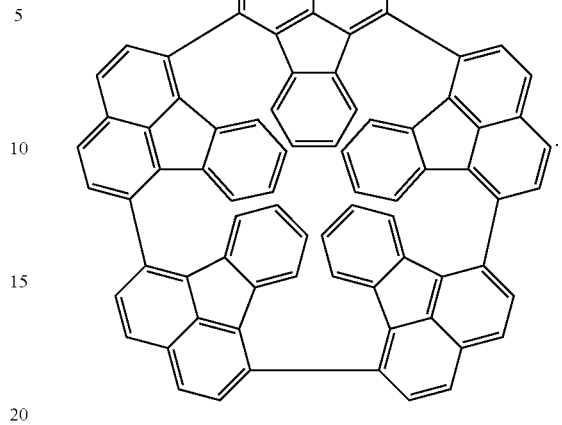

(V)

In some embodiments, at least a portion of the fluoranthene units (e.g., one, two, three, four, five, six, seven, or more of the fluoranthene units) in the oligofluoranthene each include one or two carbon-carbon bonds linking with one or two other fluoranthene units. In some embodiments, all of the fluoranthene units in the oligofluoranthene each include one or two carbon-carbon bonds linking with one or two other fluoranthene units. In some embodiments, all of the fluoranthene units in the oligofluoranthene each include two carbon-carbon bonds linking with one or two other fluoranthene units.

In some embodiments, at least a portion of the fluoranthene units (e.g., one, two, three, four, five, six, seven, or more of the fluoranthene units) in the oligofluoranthene each include two or more carbon-carbon bonds linking with one, two, or more other fluoranthene units, where each carbon-carbon bond is attached on each fluoranthene unit at a carbon position independently selected from 1, 4, 5, 7, 8, and 10.

In some embodiments, at least a portion of the fluoranthene units (e.g., one, two, three, four, five, six, seven, or more of the fluoranthene units) in the oligofluoranthene each include two or more carbon-carbon bonds linking with one, two, or more other fluoranthene units, where each carbon-carbon bond is attached on each fluoranthene unit at a carbon position independently selected from 5, 7, 8, and 10.

In some embodiments, at least a portion of the fluoranthene units (e.g., one, two, three, four, five, six, seven, or more of the fluoranthene units) in the oligofluoranthene each include two carbon-carbon bonds linking with one or two other fluoranthene units, where each carbon-carbon bond is attached on each fluoranthene unit at a carbon position independently selected from 5 and 10. As one example, the oligofluoranthene can include one or more fluoranthene units represented by Formula III:

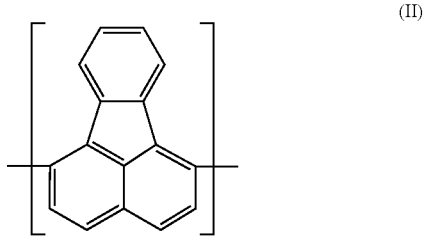

(II)

In some embodiments, at least a portion of the fluoranthene units (e.g., one, two, three, four, five, six, seven, or more of the fluoranthene units) in the oligofluoranthene each include two carbon-carbon bonds linking with one or two other fluoranthene units, where each carbon-carbon bond is attached on each fluoranthene unit at a carbon position independently selected from 7 and 8. As one example, the oligofluoranthene can include one ore more fluoranthene units represented by Formula III:

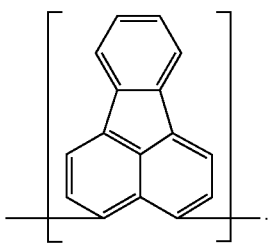

(III)

The one or more oligofluoranthenes in the composition may, in some embodiments, be selected from compounds represented by the chemical formula $C_{16m}H_{8m}$, where m is an integer greater than one (e.g., 2, 3, 4, 5, or more). In some embodiments, m can be 2, 3, 4, 5, 6, 7, 8, 9, or 10. In some embodiments, m can be 2, 3, 4, or 5. Non-limiting examples of chemical formulas that may represent one or more oligofluoranthenes in the composition include $C_{32}H_{16}$, $C_{48}H_{24}$, $C_{64}H_{32}$, $C_{80}H_{40}$, $C_{96}H_{48}$, $C_{112}H_{56}$, $C_{128}H_{64}$, $C_{144}H_{72}$, and $C_{160}H_{88}$.

In some embodiments, the oligofluoranthene include fluoranthene units bonded together to form a macrocyclic compound. For example, the compound of Formula V includes a macrocyclic ring. In some embodiments, the macrocyclic ring has nine or more carbon atoms. In some embodiments, the macrocyclic ring has fourteen or more carbon atoms.

The total amount of fluoranthene units in each oligofluoranthene can vary. Each oligofluoranthene can include, for example, two, three, four, five, six, seven, or more fluoranthene units. In some embodiments, only fluoranthene units are incorporated into the oligofluoranthene. That is, no other monomer units, such as pyrrole, are linked (e.g., covalently bonded) with the fluoranthene units in the oligofluoranthene. In some embodiments, the oligofluoranthene consists of fluoranthene units.

The total amount of the one or more oligofluoranthenes in the composition is not particularly limited and can vary depending upon the desired use. For example, a relatively small amount of one or more oligofluoranthenes can be used for certain fluorescence applications that are discussed further below. The total amount of the one or more oligofluoranthenes may, for example, be at least about 1 ppm; at least about 10 ppm; at least about 50 ppm; at least about 1% by weight; at least about 2% by weight; or at least about 5% by weight. The total amount of the one or more oligofluoranthenes may, for example, be less than or equal to about 99% by weight; less than or equal to about 90% by weight; less than or equal to about 50% by weight; less than or equal to about 10% by weight; less than or equal to about 1% by weight; less than or equal to about 500 ppm.

It will be appreciated that the "total amount" of the one or more oligofluoranthenes can include the combined amount of two or more different oligofluoranthene compounds. For example, the total amount of the one or more oligofluoranthenes can be the combined amount of oligofluoranthenes represented by the chemical formulas $C_{32}H_{16}$ and $C_{80}H_{40}$. The total amount of the one or more oligofluoranthenes may also be expressly limited to one ore more specific compounds (or a sub-genus of compounds) disclosed in the present application.

In some embodiments, the one or more oligofluoranthenes that may be in the composition include periflanthene, a compound represented by Formula IV, a compound represented by Formula V, a compound represented by Formula VI, and a compound of Formula VII:

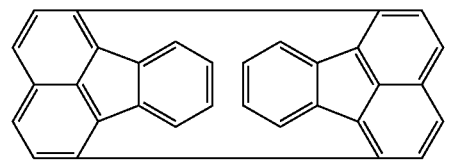

(IV)

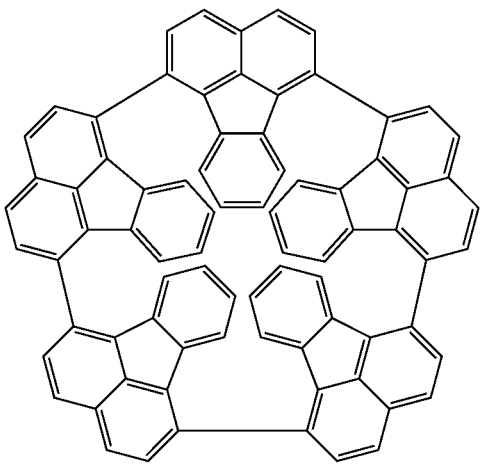

(V)

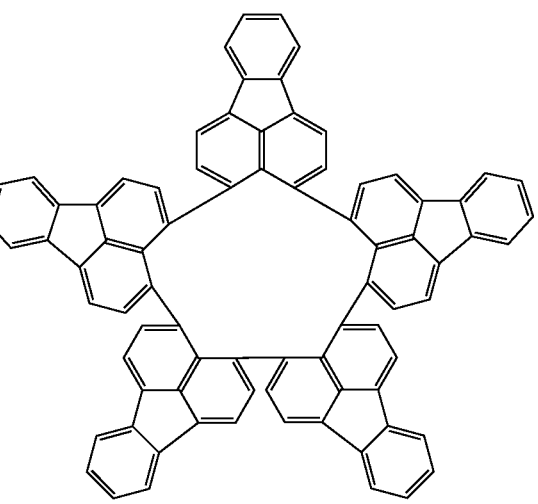

(VI)

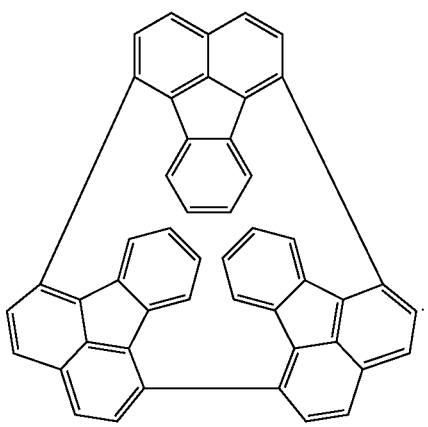

(VII)

The composition can also include, in some embodiments, two or more (e.g., two, three, four, or more) oligofluoranthenes. The two or more oligofluoranthenes can be any of those disclosed in the present application. For example, the composition may include a compound represented by Formula IV and a compound represented by Formula VI. In some embodiments, the composition includes two or more (e.g., two, three, four, or more) oligofluoranthenes that are each compounds represented by different chemical formulas. The chemical formulas can be, for example, two or more selected from $C_{32}H_{16}$, $C_{48}H_{24}$, $C_{64}H_{32}$, $C_{80}H_{40}$, $C_{96}H_{48}$, $C_{112}H_{56}$, $C_{128}H_{64}$, $C_{144}H_{72}$, or $C_{160}H_{88}$. In some embodiments, the composition includes two or more (e.g., two, three, four, or more) oligofluoranthenes that are each different compounds selected from periflanthene, a compound represented by Formula IV, a compound represented by Formula V, a compound represented by Formula VI and a compound of Formula VII.

The composition may be a liquid that includes the one or more oligofluoranthenes. For example, the one or more oligofluoranthenes can be dispersed (e.g., dissolved) in a solvent. The solvent can be an organic solvent or water. The organic solvent may, for example, be a non-polar solvent, a polar aprotic solvent, a polar protic solvent, or combinations thereof. In some embodiments, the composition includes a polar aprotic solvent. Non-limiting examples of aprotic solvents include n-methyl-2-pyrrolidone (NMP), dimethylformamide (DMF), dimethylacetamide (DMA) and dimethyl sulfoxide (DMS). The amount of solvent in the composition can be, for example, at least about 30% by weight; at least about 50% by weight; at least about 70% by weight; at least about 90% by weight; or at least about 95% by weight.

The composition may, in some embodiments, be a solid. For example, a solid form of the oligofluoranthene may be obtained by precipitating or drying the oligofluoranthene from solution (e.g., solvent casting). The solid composition may include amorphous or semi-crystalline forms of the oligofluoranthene. In some embodiments, the one or more oligofluoranthenes are blended with one or more polymers. Generally, any inert polymer may be blended with the oligofluoranthenes; such inert polymers can be, for example, acrylics, polyolefins, polyamides, polyesters, polysulfones, fluoropolymers, vinyl polymers, and the like. For example, the composition can be a blend of a compound of Formula IV and polysulfone. This blend can by prepared, for example, by solvent casting to form a film. The amount of the polymer in the composition is not particularly limited and can be, for example, at least about 10% by weight; at least about 30% by weight; at least about 70% by weight; at least about 90% by weight; at least about 95% by weight; at least about 97% by weight; or at least about 99% by weight.

The composition may, in some embodiments, exhibit electrical conductivity when doped with an effective amount of dopant. For example, the composition can exhibit a conductivity of about $1.02 \cdot 10^{-4}$ S·cm$^{-1}$ when doped with iodine vapor. In some embodiments, the composition exhibits a conductivity of at least about $10^{-10}$ S·cm$^{-1}$ when doped with an effective amount of dopant. In some embodiments, the composition exhibits a conductivity of at least about $10^{-9}$ S·cm$^{-1}$ when doped with an effective amount of dopant. In some embodiments, the composition exhibits a conductivity of at least about $10^{-8}$ S·cm$^{-1}$ when doped with an effective amount of dopant. In some embodiments, the composition exhibits a conductivity of at least about $10^{-7}$ S·cm$^{-1}$ when doped with an effective amount of dopant. In some embodiments, the composition exhibits a conductivity of at least about $10^{-6}$ S·cm$^{-1}$ when doped with an effective amount of dopant. In some embodiments, the composition exhibits a conductivity of at least about $10^{-5}$ S·cm$^{-1}$ when doped with an effective amount of dopant. Non-limiting examples of dopants include halogenated compounds, such as iodine, bromine, chlorine, iodine trichloride; protonic acids such as sulfuric acid, hydrochloric acid, nitric acid, perchloric acid; Lewis acids, such as aluminum trichloride, ferric trichloride, molybdenum chloride; and organic acids, such acetic acid, trifluoracetic acid, and benzenesulfonic acid. In some embodiments, the dopant is iodine.

The composition can also exhibit fluorescence when exposed to radiation. In some embodiments, the composition may exhibit green or blue emission when exposed to blue or ultraviolet radiation. The green or blue emission may, for example, have a wavelength of peak emission of about 450 nm to about 550 nm. In some embodiments, the green or blue emission has a wavelength of peak emission of about 475 nm to about 525 nm. The blue or ultraviolet radiation may, for example, have a peak wavelength of about 350 nm to about 450 nm.

In some embodiments, the one or more oligofluoranthenes in the composition exhibit superior fluorescence relative to fluoranthene. For example, the one or more oligofluoranthenes may exhibit a peak emission intensity that is at least about five times greater than a peak emission intensity for fluoranthene when exposed to ultraviolet or violet radiation. In some embodiments, the one or more oligofluoranthenes may exhibit a peak emission intensity that is at least about eight times greater than a peak emission intensity for fluoranthene when exposed to ultraviolet or violet radiation. In some embodiments, the one or more oligofluoranthenes may exhibit a peak emission intensity that is at least about ten times greater than the peak emission intensity for fluoranthene when exposed to ultraviolet or violet radiation. The blue or ultraviolet radiation may, for example, have a peak wavelength of about 350 nm to about 450 nm. A relative comparison between the oligofluoranthenes can be made using similar concentrations of each compound in separate solutions of N-methyl-2-pyrrolidone.

Method of Making Compositions Including Oligofluoranthene

Some embodiments disclosed herein include a method of making one or more oligofluoranthenes. Any of the oligofluoranthenes described in the present application may be prepared using this process. The method can include, for example, forming a composition comprising an oxidizing agent and fluoranthene; and maintaining the composition under conditions effective to covalently bond two or more fluoranthenes to form one or more oligofluoranthenes.

The operation of forming the composition is not particularly limited. Any suitable method of combining the ingredients is within the scope of the present application. For example, the oxidizing agent can be combined (e.g., mixed or dissolved) in a first solvent, and fluoranthene can be combined (e.g., mixed or dissolved) in a second solvent. The solution may then be combined by dropwise or continuous addition of one of the mixtures to the other. The first and second solvents may be the same or different. In some embodiments, the first solvent is at least partially immiscible in the second solvent. In some embodiments, the oxidizing agent is soluble in the first solvent. In some embodiments, fluoranthene is soluble in both the first and second solvents. Non-limiting examples for the first solvent include nitromethane, nitroethane, and propylene carbonate. Non-limiting examples for the second solvent include nitromethane, nitroethane, hexane, and chloroform.

Without being bound to any particular theory, it is believed that the oligofluoranthene is formed by dehydrogen coupling between two or more fluoranthenes. Thus, oxidative agents that can dehydrogenate and dissolve in the solvent system (e.g., nitromethane) without excessive side-reactions could be selected as the oxidizing agent. In some embodiments, the oxidizing agent is a Lewis acid. Examples of suitable oxidizing agents include, but are not limited to, $FeCl_3$, $AlCl_3$, $MoCl_5$ and $CuCl_2$.

The molar ratio of the oxidizing agent to fluoranthene in the composition can be, for example, at least about 3:1; at least about 4:1; at least about 5:1; or at least about 7:1. The molar ratio of the oxidizing agent to the total amount of monomer components in the composition can be, for example, less than or equal to about 20:1; less than equal to about 15:1; less than or equal to about 12:1; less than equal to about 10:1; or less than equal to about 9:1.

In some embodiments, at least about 90% by weight of the total amount of aromatic compounds in the composition are fluoranthene. In some embodiments, at least about 95% by weight of the total amount of aromatic compounds in the composition are fluoranthene. In some embodiments, at least about 99% by weight of the total amount of aromatic compounds in the composition are fluoranthene. In some embodiments, substantially all of the total amount of aromatic compounds in the composition is fluoranthene. In some embodiments, the composition does not include pyrrole.

After forming the composition having the oxidizing agent and fluoranthene, the composition can be maintained at conditions effective to form the oligofluoranthene. For example, the composition can be maintained at about atmospheric pressure and a temperature of about 30° C. to about 80° C. In some embodiments, the temperature can be about 40° C. to about 60° C. In some embodiments, the temperature can be about 45° C. to about 55° C. Specific examples of temperatures include about 35° C., about 40° C., about 45° C., about 50° C., about 55° C., about 60° C., about 65° C., about 70° C., and ranges between any two of these values. The composition may be maintained at the conditions for a period of time sufficient to obtain the oligofluoranthene. The composition, for example, may be maintained at the conditions for at least about 1 hour; at least about 3 hours; at least about 5 hours; at least about 10 hours; at least about 15 hours; at least about 20 hours; at least about 30 hours. The composition, for example, may be maintained at the conditions for less than or equal to about 100 hours; less than or equal to about 50 hours; less than or equal to about 30 hours; or less than or equal to about 20 hours.

The method may also optionally include isolating the oligofluoranthene from the composition. For example, the oligofluoranthene may be isolated by centrifuging the composition to obtain one or more oligofluoranthenes within the precipitate. The oligofluoranthene may be subject to various other optional treatments, such as washing, doping, dedoping, and the like.

The yield of the one or more oligofluoranthenes using the method will vary depending upon various factors, such as the temperature and the like. In some embodiments, the method yields at least about 40% by weight of the one or more oligofluoranthenes relative to a total amount of fluoranthene in the composition. In some embodiments, the method yields at least about 60% by weight of the one or more oligofluoranthenes relative to a total amount of fluoranthene in the composition. In some embodiments, the method yields at least about 70% by weight of the one or more oligofluoranthenes relative to a total amount of fluoranthene in the composition. In some embodiments, the method yields at least about 80% by weight of the one or more oligofluoranthenes relative to a total amount of fluoranthene in the composition.

Methods and Apparatuses for Emitting Light

Some embodiments of the present application include methods and apparatuses for producing light.

A method of producing light can include exposing a composition to a blue or ultraviolet radiation, where the composition includes one or more oligofluoranthenes. In some embodiments, at least one of the oligofluoranthenes is not periflanthene. The method of producing light can include any of the compositions described in this application. The blue or ultraviolet radiation may, for example, have a peak wavelength of about 350 nm to about 450 nm. In some embodiments, the method produces blue or green light. For example, the blue or green emission may have a wavelength of peak emission of about 450 nm to about 550 nm. In some embodiments, the blue or green emission may have a wavelength of peak emission of about 475 nm to about 525 nm FIG. 1 depicts an illustrative embodiment of a lighting apparatus that is within the scope of the present application. Lighting apparatus 100 includes substrate 110 having a light source 120 disposed above substrate 110. The light source can be coupled to an electric source and configured to emit blue or ultraviolet radiation. For example, the light source can be an indium gallium nitride (InGaN) semiconductor. Composition 130 is disposed above light source 120 and configured to receive at least a portion of the radiation from light source 120. Composition 130 can be a powder dispersed in encapsulant resin 140. For example, encapsulant resin 140 may be an epoxy. As an alternative, the composition can be a film disposed above the light source (not shown).

In some embodiments, the apparatus includes: a light source configured to emit an ultraviolet or blue radiation; and a composition configured to receive at least a portion of the radiation emitted from the light source, where the composition includes one or more oligofluoranthenes. The composition may include one or more oligofluoranthenes as described in this application.

The oligofluoranthene compositions of the present application may also be included in an organic light emitting diode (OLED). OLEDs are well-known in the art. For example, U.S. Pat. No. 6,322, 910 discloses various configurations for OLEDs. A typical OLED can include a light emitting layer disposed between a cathode and anode. A current flow between the cathode and anode can result in electrons recombining with electron holes in the light emitting layer. This recombination can result in emission. Thus, for example, the light emitting layer can include any of the oligofluoranthene compositions described in the present application. In some embodiments, the OLED can include multiple emissive layers.

Figure 2:
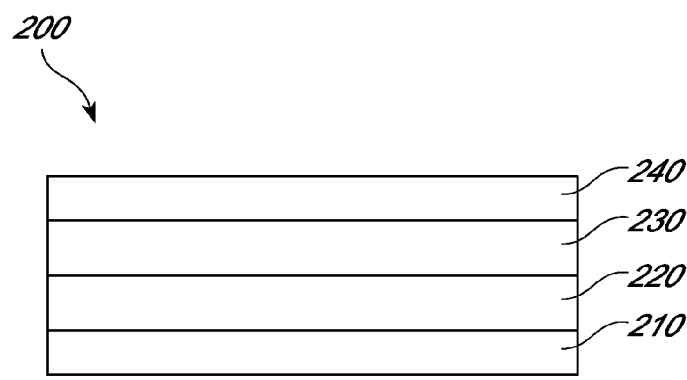
FIG. 2 is an illustrative embodiment of an organic light emitting diode that is within the scope of the present application (not to scale).

FIG. 2 is an illustrative embodiment of an organic light emitting diode that is within the scope of the present application. OLED 200 includes anode 210 having conducting layer 220 above anode 210. Emissive layer 230 is disposed between conductive layer 220 and cathode 240. The anode can be, for example, indium tin oxide (ITO), which can optionally be disposed on a transparent substrate (e.g., glass) (not shown). Meanwhile, metals with low work functions, such as barium or calcium, can be used to form the cathode. The conductive layer can be a conductive polymer, such as poly(3,4-ethylenedioxythiophene) poly(styrenesulfonate) (PEDOT:PSS). The emissive layer may include any of the oligofluoranthene compositions described in the present application.

Methods and Apparatuses for Detecting Nitroaromatics

Some embodiments of the present application include methods and apparatuses for detecting nitroaromatics. Without being bound to any particular theory, it is believed that nitroaromatics can quench fluorescence of the oligofluoranthene compositions described in the present application. Thus, if the composition exhibits reduced fluorescence, this may be correlated with exposing the composition to a nitroaromatic.

Non-limiting examples of nitroaromatics that may be detected using the methods and apparatuses disclosed in the present application include picric acid, nitrobenzene, dinitrobenzene, nitrotoluene, TNT (3,4,6-trinitrotoluene), DNT (2, 4-dinitrotoluene), nitrophenol, 1,3,5-trinitrobenzene (TNB), and 2,6-dinitrobenzonitrile (DNB).

In some embodiments, a method for detecting nitroaromatics includes: (a) providing a sample suspected of containing one or more nitroaromatics; (b) contacting the sample with a composition having one or more oligofluoranthenes; (c) exposing the composition to a radiation effective to produce fluorescence from the composition; and (d) measuring the amount of fluorescence produced by the composition. The composition can be any of the oligofluoranthene compositions described in the present application. For example, the composition may include the compound of Formula IV disclosed above.

In some embodiments, the produced fluorescence is greater in the absence of nitroaromatics than in the presence of nitroaromatics. The fluorescence can be measured, for example, by measuring the fluorescence intensity at a predetermined color or wavelength. For example, the intensity of emission at a wavelength of about 490 nm can be measured. In some embodiments, the radiation effective to produce fluorescence from the composition is a blue or ultraviolet radiation.

Figure 3:
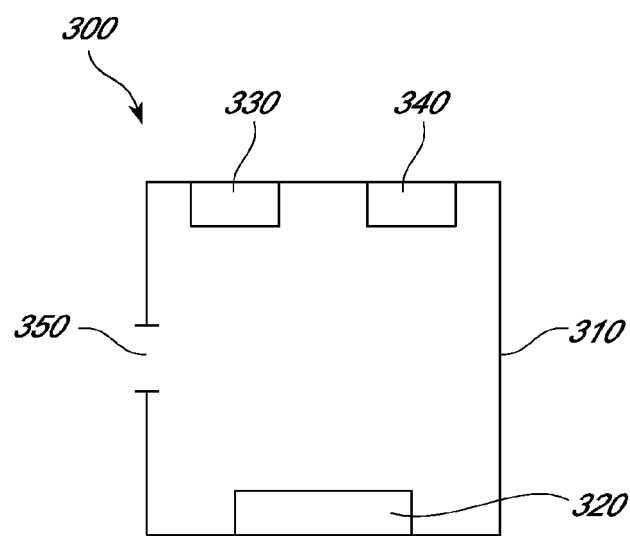
FIG. 3 depicts an illustrative embodiment of an apparatus for detecting nitroaromatics that is within the scope of the present application (not to scale).

FIG. 3 depicts an illustrative embodiment of an apparatus for detecting nitroaromatics that is within the scope of the present application. Apparatus 300 can include housing 310 that contains composition 320, light source 330, light detector 340, and port 350. Composition 320 can include any of the oligofluoranthene compositions described in the present application. Light source 330 is configured to emit radiation effective to produce fluorescence from copolymer film 320. For example, light source 330 can be an InGaN semiconductor that emits blue or ultraviolet radiation. Light detector 340 can be configured to measure light emission from composition 320. Port 350 can be configured to receive a sample into the housing. Thus, for example, a sample suspected of containing one or more nitroaromatics may be placed into housing 310 via port 350, so that the sample contacts composition 320. Light source 330 may then emit light and the fluorescence from composition 320 is detected by light detector 340. The amount of fluorescence may then be correlated with the presence of nitroaromatics in the sample.

In some embodiments, the apparatus for detecting nitroaromatics includes a processor coupled to at least the light source and light detector (not shown). The processor may be configured to synchronize both emitting light from the light source and detecting fluorescence with the light detector. The processor may also receive measurement data from the light detector and automatically correlate this data with the presence of nitroaromatics.

EXAMPLES

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Example 1

Preparing Oligofluoranthenes

Oligofluoranthenes were prepared by chemical oxidation using one or more oxidizing agents in nitromethane at 50° C.

A typical procedure included adding fluoranthene (4 mmol) in nitromethane (20 mL) dropwise to $FeCl_3$ (20 mmol) solution in nitromethane (20 mL). The resulting mixture was maintained at 50° C. in a water bath with constant stirring for 15 hours. As soon as the fluoranthene solution was added, the reaction mixture turned a dark color and solid particles were obtained. After reaction, the precipitate was isolated by centrifugation and washed with an excess of ethanol and distilled water until the top layer liquid in the centrifuge tubes became colorless. After that, the liquid was tested for residual $Fe^{2+}$ and $Fe^{3+}$ by adding potassium ferricyanide and potassium ferrocyanide to a sample of the aqueous solution. The sample did not exhibit a blue color; therefore, the sample included very low amounts of $Fe^{2+}$ and $Fe^{3+}$. Then HCl was used to replace trace amounts of $FeCl_3$ and $FeCl_2$ (reduction product of $FeCl_3$) on the oligofluoranthenes. Subsequently, ammonia was employed to remove the HCl remaining and a powder was obtained after drying under an IR lamp.

The same procedures were repeated except that the oxidizing agent was ammonium persulfate, sulfuric acid, or a combination of equal parts ammonium persulfate and sulfuric acid.

Figure 4:
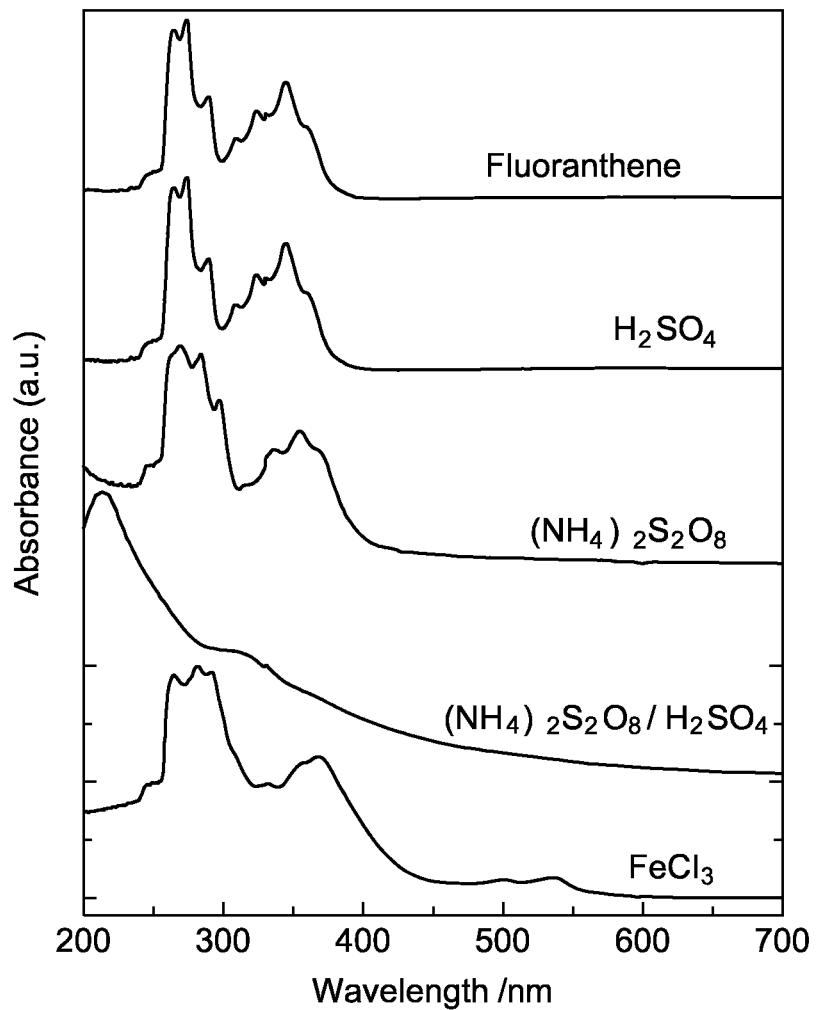
FIG. 4 shows the UV-visible absorbance spectra for oligofluoranthene compositions prepared with various oxidizing agents.

The UV-Visible absorption spectra for each composition were measured on a Lambda 35 UV-Vis spectrophotometer between 200 and 900 nm in NMP. The results are shown in FIG. 4. The compositions prepared with $FeCl_3$ show new absorptions at 499 nm and 537 nm which may be associated large π-π conjugations. In contrast, compositions obtained with ammonium persulfate and sulfuric acid did not exhibit the same absorption.

These results suggest that $FeCl_3$ effectively produced oligofluoranthenes with covalent bonding between fluoranthene units. These oligofluoranthenes may also exhibit a larger conjugated pi system. The other oxidizing agents produced compositions that may not include oligofluoranthenes. This suggests that oxidizing agents that are Lewis acids may improve the oxidative oligomerization via dehydrogen of fluoranthene.

Example 2

Modifying Amount of Oxidizing Agent

Additional compositions were prepared using generally the same procedures describe in Example 1 with $FeCl_3$ as the oxidizing agent. However, in one set of experiments the molar ratio of $FeCl_3$ to fluoranthene was 3:1, 5:1, 7:1, 9:1, 12:1, or 15:1 to form the composition having one or more oligofluoranthenes.

The conductivity of each composition was also studied. Each composition and sufficient $I_2$ particles were kept in a sealed tube at 80° C. under atmospheric pressure for a week. The powder did not directly contact the $I_2$ particles. After $I_2$ vapor doping, the composition turned to black. The bulk electrical conductivity of the composition after doping was measured by a two-electrode method using a UT70 A multimeter at ambient temperature.

The yield and conductivity for each composition obtained is shown in Table 1. The yield increased with the amount of oxidizing agent but appears to plateau at a ratio of about 9:1. Meanwhile, the conductivity was highest at about 5:1. These results suggest that an excess amount of oxidizing agent may decrease the amount of π-conjugated bonds in the oligofluoranthene.

TABLE 1

Yield and Conductivity for Various Amounts of Oxidizing Agent

| Molar Ratio of $FeCl_3$ to fluoranthene | Yield (%) | $I_2$-doped Conductivity (S/cm) |
|---|---|---|
| 3:1 | 31.0 | $7.12 \times 10^{-6}$ |
| 5:1 | 68.5 | $1.03 \times 10^{-4}$ |
| 7:1 | 83.5 | $4.64 \times 10^{-5}$ |
| 9:1 | 90.5 | $7.80 \times 10^{-6}$ |
| 12:1 | 82.4 | $3.90 \times 10^{-6}$ |
| 15:1 | 79.7 | $9.02 \times 10^{-7}$ |

Figure 5:
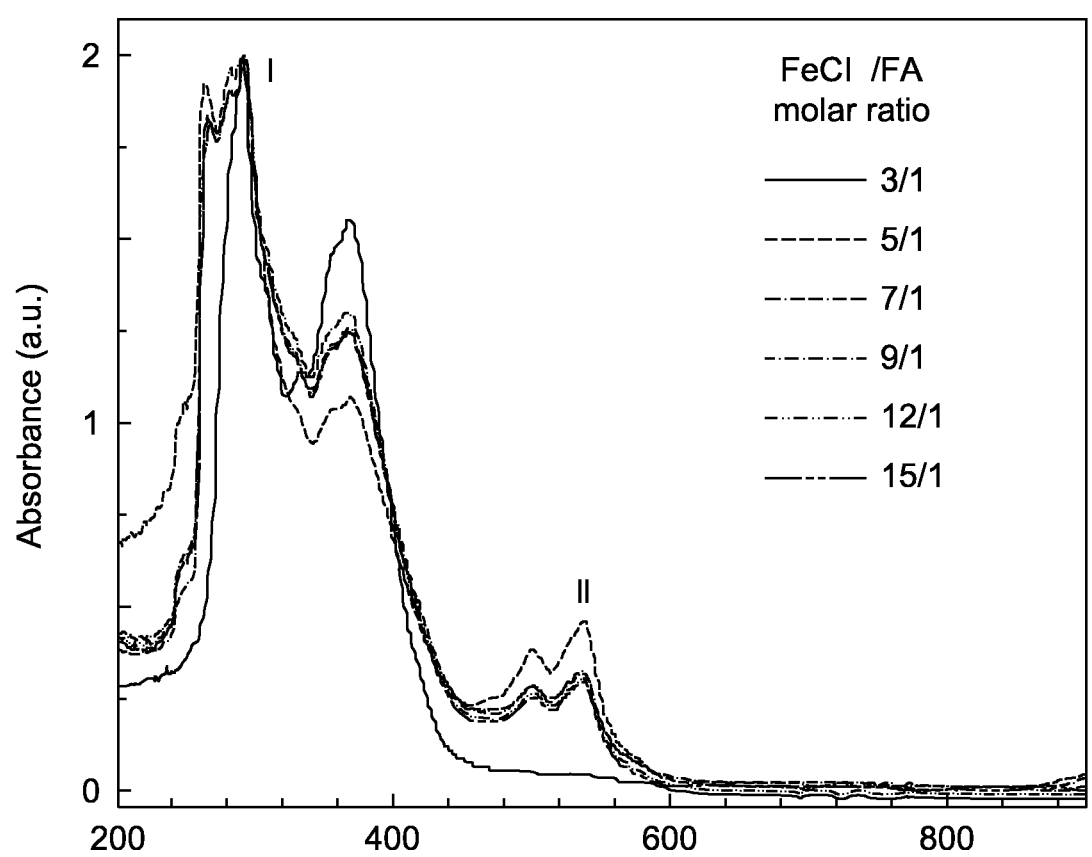
FIG. 5 shows the UV-visible absorbance spectra for oligofluoranthene compositions prepared using different molar ratios of $FeCl_3$ to fluoranthene.

The UV-Visible absorption spectra for each composition was measured as described in Example 1 and are shown in FIG. 5. The 3:1 molar ration did not produce Band II in the spectra. These results suggest a ratio of oxidizing agent to fluoranthene of more than 3:1 can produce covalent bonds between fluoranthene units and a larger conjugated pi system.

Figure 6:
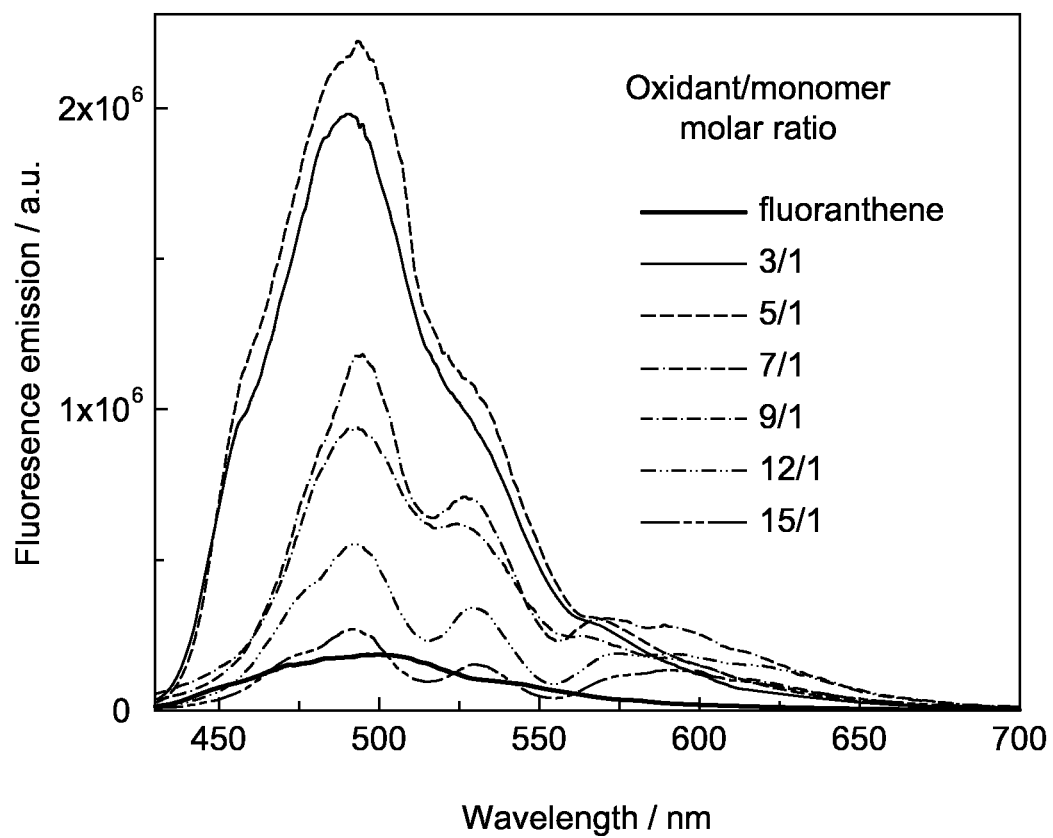
FIG. 6 shows the fluorescence emission for oligofluoranthene compositions obtained using different molar ratios of $FeCl_3$ to fluoranthene. The compositions were excited at 395 nm.

The fluorescence excitation and emission spectra of the compositions were obtained at slit widths of 2.5 nm using a F-7000 FL Spectrophotometer. FIG. 6 shows the emission for each composition obtained with varying amounts of $FeCl_3$ when excited at 395 nm. The results suggest that excess amounts of oxidizing agent can reduce the fluorescence of the oligofluoranthene. This may result from excessive oxidation of the fluoranthene units.

Most interestingly, the fluorescence emission for the 5:1 ratio was dramatically enhanced relative to fluoranthene (about 12 times greater).

Example 3

Modifying Temperature

Additional compositions were prepared using generally the same procedures describe in Example 1 with $FeCl_3$ as the oxidizing agent. However, the reaction temperature was maintained at 30° C., 50° C., 60° C., 70° C., or 80° C.

Figure 7:
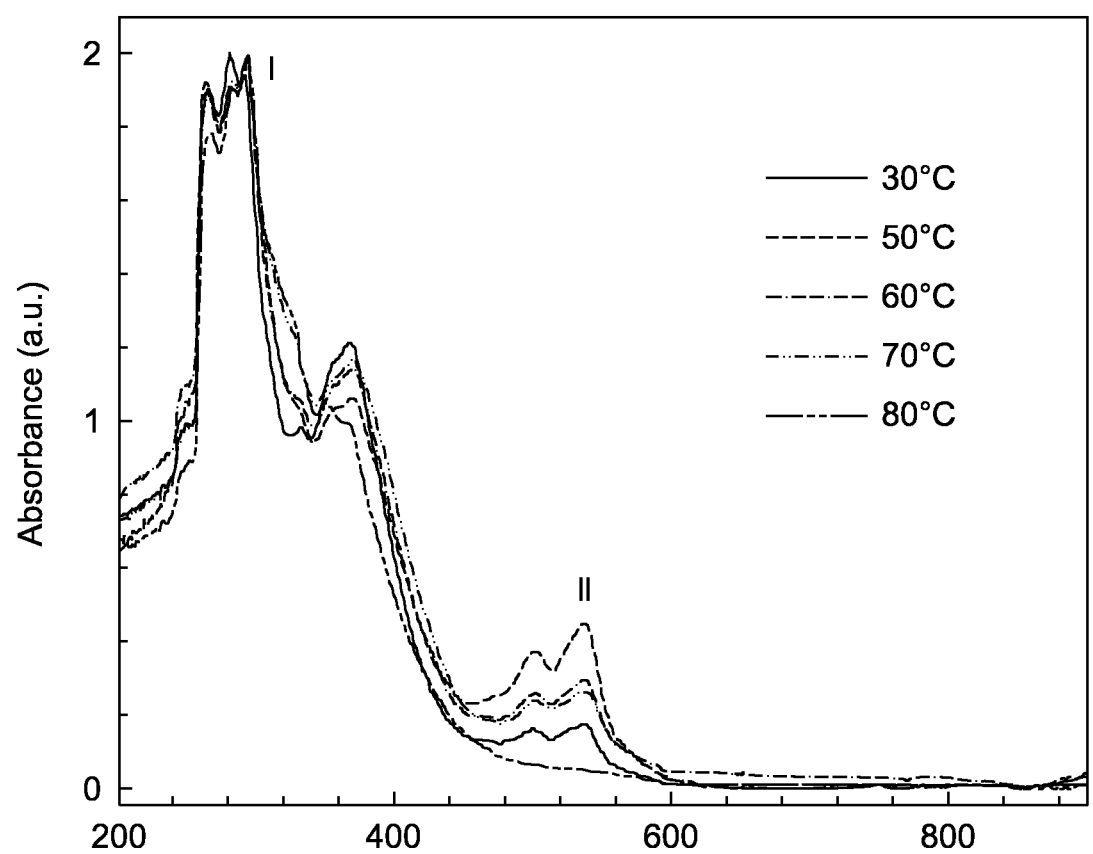
FIG. 7 shows the UV-visible absorbance spectra for oligofluoranthene compositions obtained using $FeCl_3$ at varying reaction temperatures.

The conductivity of each resulting composition was determined using the same procedures described in Example 2. The conductivity and yield are shown in Table 2. The UV-Visible absorption spectra for each composition was measured as described in Example 1 and are shown in FIG. 7.

TABLE 2

Yield and Conductivity for Various Amounts of Oxidizing Agent

| Temperature (° C.) | Yield (%) | $I_2$-doped Conductivity (S/cm) |
|---|---|---|
| 30 | 61.1 | $1.52 \cdot 10^{-9}$ |
| 50 | 68.5 | $1.02 \cdot 10^{-4}$ |
| 60 | 63.2 | $5.88 \cdot 10^{-7}$ |
| 70 | 61.4 | $1.88 \cdot 10^{-9}$ |
| 80 | 26.3 | $9.23 \cdot 10^{-10}$ |

These results suggest reactions temperature can affect the final structure of the oligofluoranthenes because both low and high temperature reactions produced compositions diminished conductivity relative to a reaction at about 50° C.

Example 4

Mass Spectrometry Analysis

Molecular weight of the composition prepared according to Example 1 using $FeCl_3$ as the oxidizing agent was determined with 2,5-dihydroxybenzoic acid as a matrix on a MALDI-TOF MS using a Voyager DE.

Figure 8:
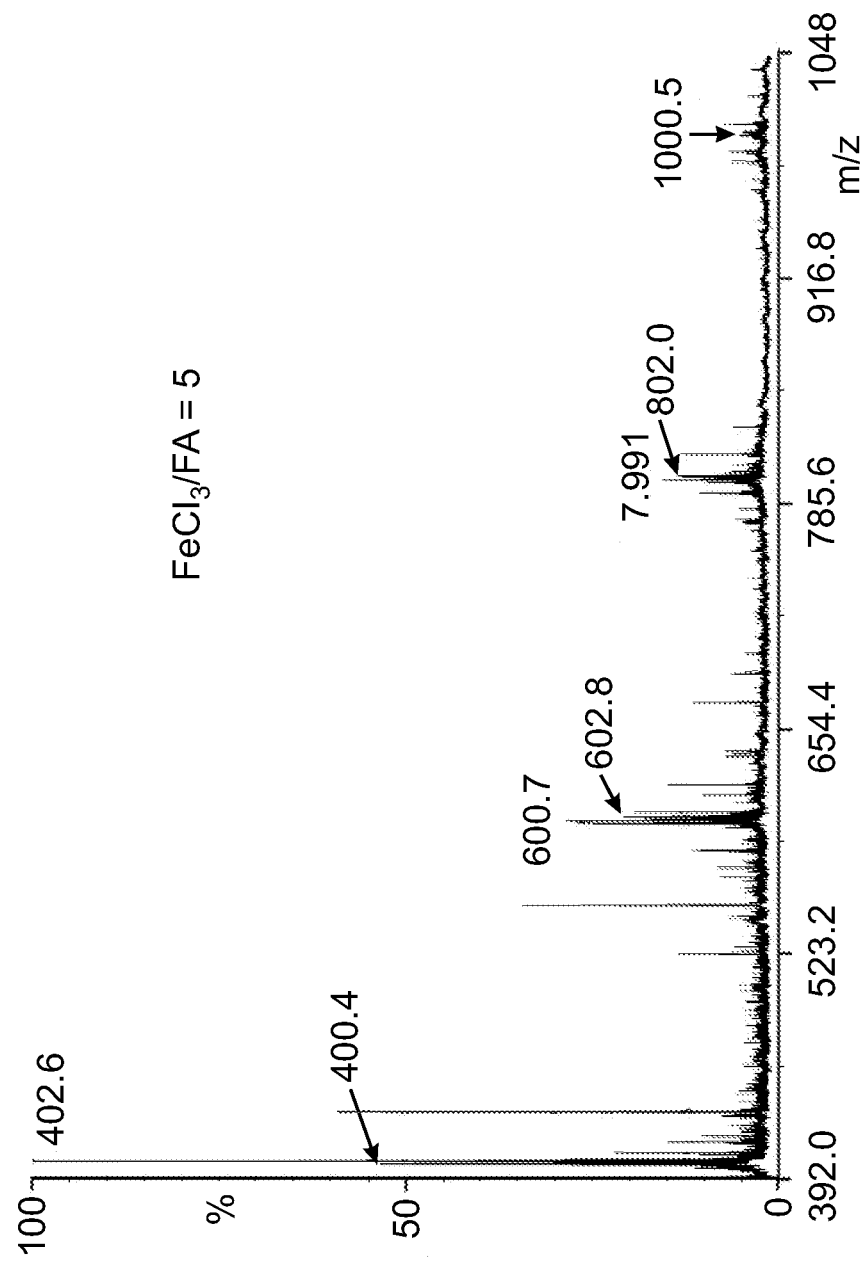
FIG. 8 shows MALDI-TOF mass spectrometry results for a composition obtained using a 5:1 molar ratio of $FeCl_3$ to fluoranthene.

The results are shown in FIG. 8 and include distinctive peaks associated with a molecular weight of 400.4 Da, 600.7 Da, and 100.5 Da. These values may be associated with compounds having a chemical formula of $C_{32}H_{16}$, $C_{48}H_{24}$, and $C_{80}H_{40}$. These results also suggest that the reaction has successfully produced oligofluoranthenes having two or more fluoranthene units.

An elemental analysis was performed for the compositions in Example 2 with a $FeCl_3$ to fluoranthene molar ratio of 3:1, 5:1, and 7:1. The results are shown in Table 2.

TABLE 3

Elemental Analysis for Compositions Obtained with Varying Amounts of $FeCl_3$

| Samples | C Exp. | C Calc. | H Exp. | H Calc. | N Exp. | Formula |
|---|---|---|---|---|---|---|
| Fluoranthene | | 95.02 | | 4.98 | | $C_{16}H_{10}$ |
| Oligofluoranthene (O/Fa = 3/1) | 87.70% | | 3.22% | | 0.15% | $C_{16}H_{6.99}$ |
| Oligofluoranthene (O/Fa = 5/1) | 94.17% | | 3.91% | | 0.06% | $C_{16}H_{7.95}$ |
| Oligofluoranthene (O/Fa = 7/1) | 90.07% | | 3.31% | | 0.12% | $C_{16}H_{7.01}$ |

These results suggest that a 5:1 molar ratio of $FeCl_3$ to fluoranthene produces oligofluoranthenes with a ratio 2 to 1 ratio of carbon to hydrogen. This suggests the oligofluoranthenes include fluoranthene units having two covalent bonds with other fluoranthene units.

Example 5

IR Spectra

Figure 9:
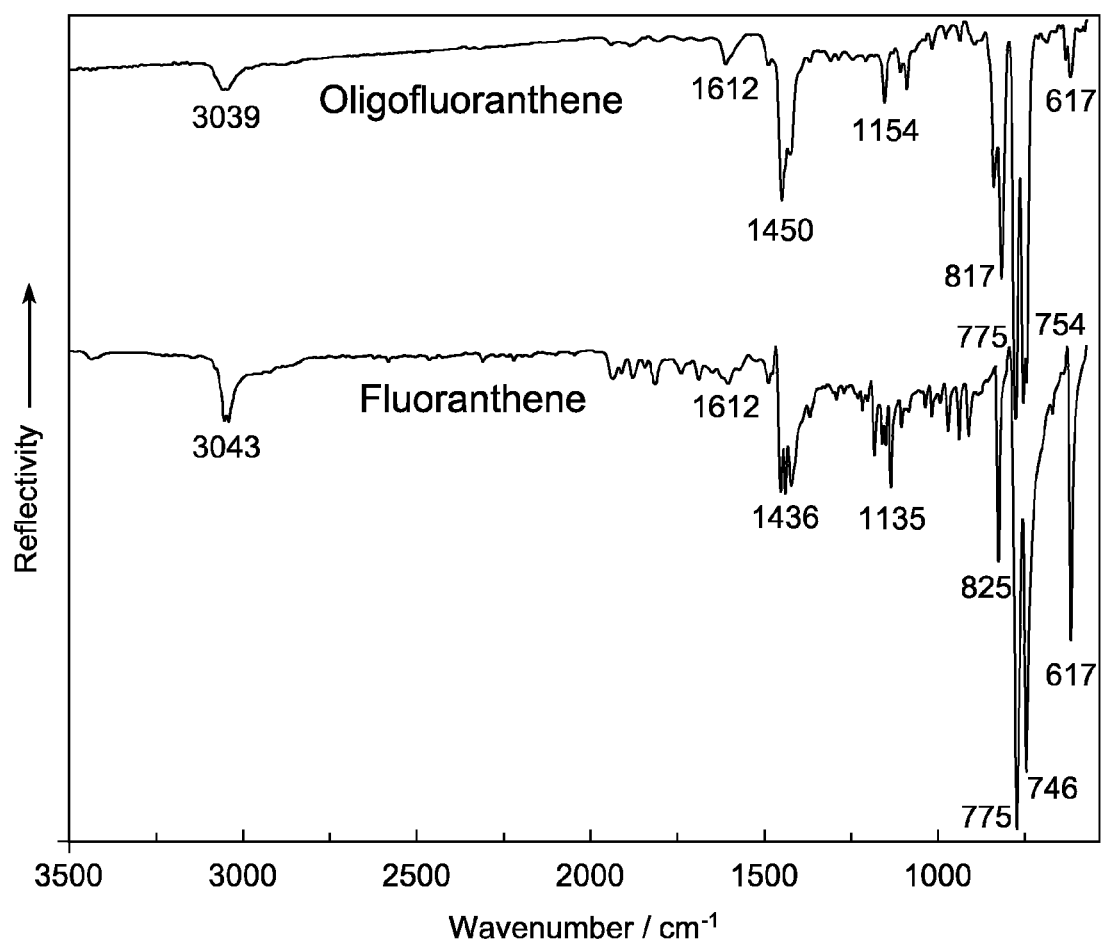
FIG. 9 shows the IR spectra for fluoranthene and oligofluoranthene compositions.

IR spectra were recorded with a Nicolet Magna-IR 550 spectrometer in a reflection mode. Representative IR reflection spectra for the composition prepared according to Example 1 using FeCl₃ as the oxidizing agent are shown in FIG. 9.

This Example demonstrates that the copolymer is structurally distinct from the fluoranthene monomer.

Example 9

Figure 10:
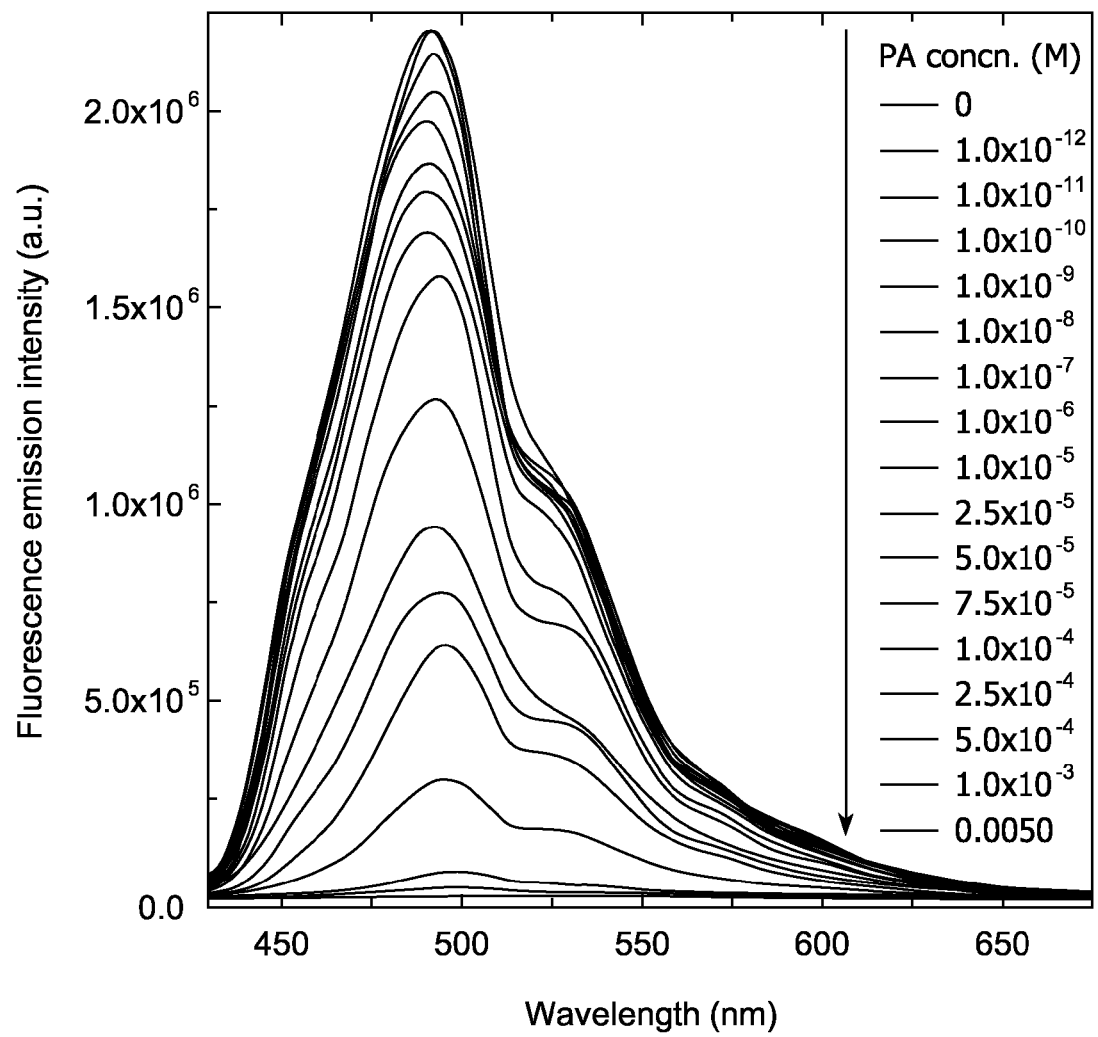
FIG. 10 shows the fluorescence spectra of a solution containing oligofluoranthenes after adding various amounts of picric acid.

Oligofluoranthene Solution for Sensing Nitroaromatic Picric Acid 10 mg/L of the composition prepared according to Example 1 using FeCl₃ as the oxidizing agent was dissolved in N-methyl-2-pyrrolidone. The solution was placed in a cuvette holder and the fluorescence spectrum was acquired at 395 nm. Incremental amounts of picric acid were added to the solution and the fluorescence measurements were repeated. FIG. 10 shows the resulting fluorescence spectra after adding various amounts of picric acid.

This Example demonstrates that the oligofluoranthene composition is quenched by nitroaromatics and the quenching is proportional to the concentration of the nitroaromatic. Accordingly, oligofluoranthene compositions can be used to detect nitroaromatics based on changes to the fluorescence spectra.

Example 10

Composite Films for Sensing Nitroaromatic Picric Acid

A composite film was prepared with the composition prepared according to Example 1 using FeCl₃ as the oxidizing agent. 0.8 parts by weight of the composition and 99.2 parts by weight of commercially available polysulfone were combined in N-methyl-2-pyrrolidone to form an 8.5% by weight solution. A glass slide was dipped into the solution and dried overnight at 50° C. overnight to obtain the composite film.

Figure 11:
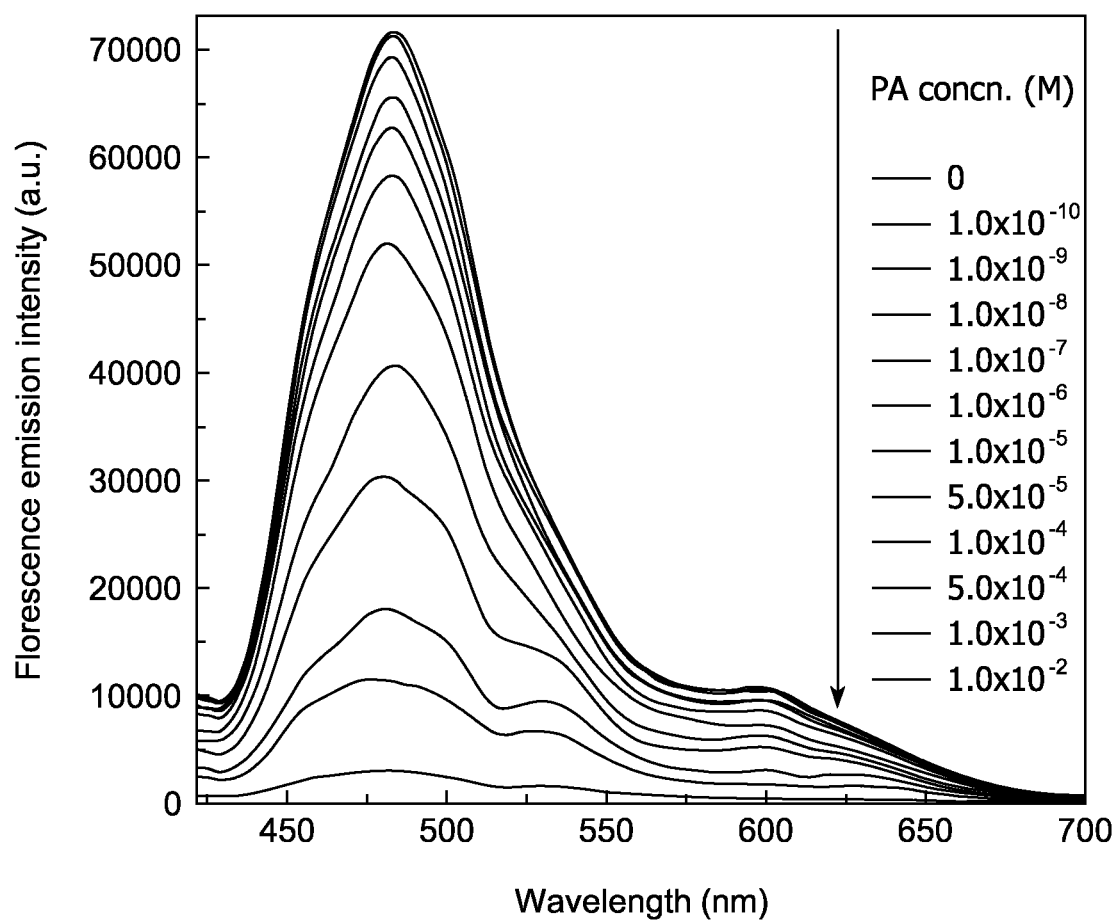
FIG. 11 shows the fluorescence spectra of an oligofluoranthene composite film. The fluorescence spectra were measured after the film contacted an aqueous solution with various concentrations of picric acid.

The fluorescence of the composite film was measured after contacting different solutions with various concentrations of picric acid. The film was washed between each measurement until the fluorescence intensity was restored. The results are shown in FIG. 11. This result demonstrates that solid forms of the copolymer can also be used to detect nitroaromatics.

Example 11

Selectivity of Compositions for Sensing Nitroaromatic Picric Acid

The selectivity of the solution in Example 9 for nitroaromatics was tested by adding 0.1 M of various molecules that could potentially interfere with fluorescence: hydrochloride, nitric acid, sulfuric acid, and perchloric acid. The solution was excited using 395 nm radiation and the fluorescence spectrum was measured. The spectra was substantially unchanged by the addition of the possible interfering molecules.

This Example demonstrates the oligofluoranthene compositions can be highly selective for detecting nitroaromatics because other molecules generally have a minimal effect on fluorescence.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., " a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., " a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells.

Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A composition comprising one or more oligofluoranthenes and at least 50% by weight of an inert polymer, wherein the one or more oligofluoranthenes each independently comprise at least two fluoranthene units represented by Formula I:

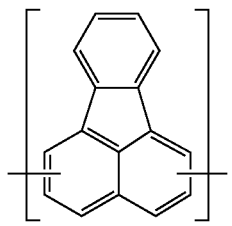

(I)

wherein at least one oligofluoranthene in the composition is not periflanthene.

2. The composition of claim 1, wherein at least one of the one or more oligofluoranthenes comprises at least three fluoranthene units represented by Formula I.

3. The composition of claim 1, wherein at least one of the one or more oligofluoranthenes comprises at least two fluoranthene units selected from the group consisting of a first unit represented by Formula II, a second unit represented by Formula III, and combinations thereof:

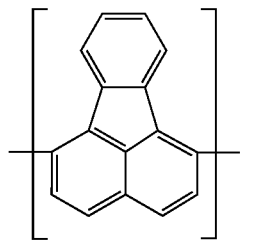

(II)

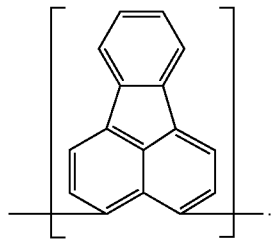

(III)

4. The composition of claim 1, wherein at least one of the one or more oligofluoranthenes has a molecular formula selected from the group consisting of $C_{32}H_{16}$, $C_{48}H_{24}$, and $C_{80}H_{40}$.

5. The composition of claim 4, wherein at least one of the one or more oligofluoranthenes has a molecular formula of $C_{32}H_{16}$.

6. The composition of claim 4, wherein at least one of the one or more oligofluoranthenes has a molecular formula of $C_{80}H_{40}$.

7. The composition of claim 4, wherein at least one of the one or more oligofluoranthenes has a molecular formula of $C_{48}H_{24}$.

8. The composition of claim 1, wherein the composition comprises at least about 1 ppm of the one or more oligofluoranthenes.

9. The composition of claim 1, wherein the composition exhibits a peak emission wavelength of about 450 nm to about 550 nm when exposed to ultraviolet or violet radiation.

10. The composition of claim 1, wherein the inert polymer is polysulfone.

11. An apparatus comprising:
at least one light source configured to emit an ultraviolet or blue radiation; and
a composition configured to receive at least a portion of the radiation emitted from the light source, wherein the composition comprises one or more oligofluoranthenes, wherein the one or more oligofluoranthenes each independently comprise at least two fluoranthene units represented by Formula I:

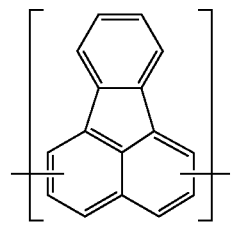

(I)

wherein at least one oligofluoranthene in the composition is not periflanthene.

12. The apparatus of claim 11, further comprising at least one light detector configured to measure light emitted from the composition.

13. The apparatus of claim 12, further comprising a processor configured to receive measurement data from the light detector and automatically correlate the measurement data with the presence of nitoraromatics.

14. The apparatus of claims 11, further comprising a housing, wherein the housing contains the composition and is configured to receive a sample.

15. The apparatus of claim 11, wherein the composition further comprises at least 50% by weight of an inert polymer.

16. An organic light-emitting diode comprising:
at least one light-emitting active layer;
at least one conducting layer on one side of the light-emitting active layer;
at least one cathode; and
at least one anode, wherein the light-emitting active layer and conducting layer are disposed between the cathode and the anode, and the light-emitting active layer comprises one or more oligofluoranthenes, wherein the one or more oligofluoranthenes each independently comprise at least two fluoranthene units represented by Formula I:

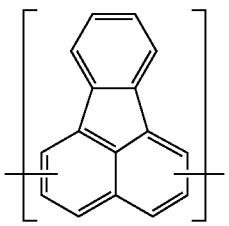

wherein at least one oligofluoranthene in the composition is not periflanthene.

17. A method of producing light comprising exposing a composition to a violet or ultraviolet radiation, wherein the composition comprises one or more oligofluoranthenes, wherein the one or more oligofluoranthenes each independently comprise at least two fluoranthene units represented by Formula I:

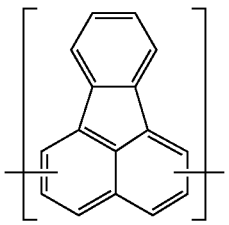

wherein at least one oligofluoranthene in the composition is not periflanthene.

18. A method for detecting nitroaromatics within a sample, the method comprising:

providing a sample suspected of containing one or more nitroaromatics;

contacting the sample with a composition comprising one or more oligofluoranthenes, wherein the one or more oligofluoranthenes each independently comprise at least two fluoranthene units represented by Formula I:

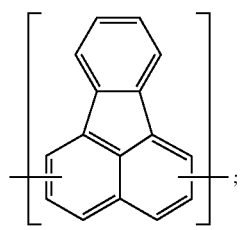

exposing the composition to a radiation effective to produce fluorescence from the composition; and measuring the amount of fluorescence produced by the composition.

19. The method of claim 18, wherein the produced fluorescence is greater in the absence of nitroaromatics than in the presence of nitroaromatics.

20. The method claim 18, wherein the one or more nitroaromatics comprise picric acid, nitrobenzene, dinitrobenzene, nitrotoluene, TNT (3,4,6-trinitrotoluene), DNT (2, 4-dinitrotoluene), nitrophenol, 1,3,5-trinitrobenzene (TNB), or 2,6-dinitrobenzonitrile (DNB).

* * * * *

UNITED STATES PATENT AND TRADEMARK OFFICE
CERTIFICATE OF CORRECTION

PATENT NO.        : 8,445,868 B2
APPLICATION NO.   : 13/503349
DATED             : May 21, 2013
INVENTOR(S)       : Li et al.

It is certified that error appears in the above-identified patent and that said Letters Patent is hereby corrected as shown below:

On the Title Page, in item (56), under "OTHER PUBLICATIONS", in Column 2, Line 3, delete "al," and insert -- al., --, therefor.

Title Page 2, in item (56), under "OTHER PUBLICATIONS", in Column 1, Line 39, delete "al-" and insert -- al., --, therefor.

Title Page 2, in item (56), under "OTHER PUBLICATIONS", in Column 2, Line 15, delete "al," and insert -- al., --, therefor.

In the Drawings

In Fig. 11, Sheet 9 of 9, delete "Florescence" and insert -- Fluorescence --, therefor.

In the Specification

In Column 14, Line 37, delete "525nm" and insert -- 525nm. --, therefor.

In Column 19, Line 7, delete "Example 9" and insert -- Example 6 --, therefor.

In Column 19, Line 26, delete "Example 10" and insert -- Example 7 --, therefor.

In Column 19, Line 44, delete "Example 11" and insert -- Example 8 --, therefor.

In Column 19, Line 49, delete "Example 9" and insert -- Example 6 --, therefor.

In the Claims

In Column 24, Line 28, in Claim 20, delete "method claim" and insert -- method of claim --, therefor.

Signed and Sealed this
Twenty-seventh Day of August, 2013

Teresa Stanek Rea
*Acting Director of the United States Patent and Trademark Office*